United States Patent [19]

Shimizu et al.

[11] Patent Number: 5,607,999
[45] Date of Patent: Mar. 4, 1997

[54] WATER-BASED RECORDING INK

[75] Inventors: Junko Shimizu; Michinari Tsukahara; Nobuyuki Yanase, all of Suwa, Japan

[73] Assignee: Seiko Epson Corporation, Tokyo-to, Japan

[21] Appl. No.: 969,808

[22] PCT Filed: May 21, 1992

[86] PCT No.: PCT/JP92/00652

§ 371 Date: Mar. 22, 1993

§ 102(e) Date: Mar. 22, 1993

[87] PCT Pub. No.: WO92/20749

PCT Pub. Date: Nov. 26, 1992

[30] Foreign Application Priority Data

| | | | |
|---|---|---|---|
| May 22, 1991 | [JP] | Japan | 3-117512 |
| Jun. 3, 1991 | [JP] | Japan | 3-130867 |
| Jul. 9, 1991 | [JP] | Japan | 3-167973 |
| Jul. 22, 1991 | [JP] | Japan | 3-180987 |
| Aug. 2, 1991 | [JP] | Japan | 3-194059 |
| Mar. 18, 1992 | [JP] | Japan | 4-062399 |
| Mar. 18, 1992 | [JP] | Japan | 4-062400 |
| Apr. 15, 1992 | [JP] | Japan | 4-095519 |

[51] Int. Cl.⁶ ................................. C08L 29/04
[52] U.S. Cl. ................ 524/503; 524/377; 524/379; 523/160; 523/161; 260/DIG. 38
[58] Field of Search ............... 524/503, 377, 524/379; 523/160, 161; 260/DIG. 38

[56] References Cited

U.S. PATENT DOCUMENTS

| | | | |
|---|---|---|---|
| 4,597,794 | 7/1986 | Ohta et al. | 523/160 |
| 4,791,165 | 12/1988 | Bearss | 524/516 |
| 5,004,763 | 4/1991 | Imagawa | 524/311 |

FOREIGN PATENT DOCUMENTS

| | | |
|---|---|---|
| 56-157468 | 12/1981 | Japan . |
| 58-63766 | 4/1983 | Japan . |
| 59-120667 | 7/1984 | Japan . |
| 2-255875 | 10/1990 | Japan . |
| 3-79680 | 4/1991 | Japan . |

OTHER PUBLICATIONS

Derwent Publications Ltd., Database WPI Week 8434, AN 84–209557 London, G.B.

*Primary Examiner*—Paul R. Michl
*Assistant Examiner*—John J. Guarriello
*Attorney, Agent, or Firm*—Ladas & Parry

[57] ABSTRACT

The water-based recording ink according to the present invention comprises water, a pigment, a water-soluble homopolymer and a copolymer having both a hydrophobic portion and a hydrophilic portion.

The ink according to the present invention can provide a print having excellent density, light fastness and water resistance. Furthermore, the water-based recording ink has such various properties necessary for use as an ink jet recording ink that it does not clog a fine ejection nozzle, has excellent rubbing resistance and setting to dry in the print, is free from aggregation or settlement of solid matter, such as a pigment particle, and exhibits no change in the properties of the ink even when stored at a high temperature or a low temperature for a long period of time and can be redispersed by stirring or further addition of a solvent even when the pigment once aggregated.

28 Claims, 1 Drawing Sheet

5,607,999

WATER-BASED RECORDING INK

BACKGROUND OF THE INVENTION

1. Technical Field

The present invention relates to a water-based ink containing a pigment as a coloring material and used for an ink jet printer wherein recording is conducted with a liquid ink.

2. Background Art

In the prior art, an ink comprising water, an organic solvent, a wax or other substance and, dissolved therein, a dye as a coloring agent has been mainly used as an ink for ink jet recording. Such an ink has poor light fastness and water resistance derived from properties of the dye. In order to solve this problem, a proposal has been made on an ink wherein a pigment, such as carbon black or aniline black, was used as the coloring agent. For example, an ink containing a water-soluble polymer in addition to the pigment is described in Japanese Patent Publication No. 15542/1989 and Japanese Patent Laid-Open Nos. 63766/1983, 255875/1990 and 276874/1990.

An ink of a water dispersion system can improve printing density, light fastness and water resistance, etc. as compared with an ink of a dye system. The ink for ink jet recording, however, should have properties such that it does not clog a fine ejection nozzle, has excellent rubbing resistance and setting to dry in the print, is free from aggregation or settlement of solid matter, such as a pigment particle, and exhibits no change in the properties of the ink even when stored at a high temperature or a low temperature for a long period of time and can be redispersed by stirring or further addition of a solvent even when the pigment once aggregated.

The above conventional inks have not yet satisfied all the property requirements of an ink jet printer.

SUMMARY OF THE INVENTION

Accordingly, an object of the present invention is to provide a water-based recording ink of a pigment system which can satisfy various property requirements of an ink jet recording ink.

A water-based recording ink according to the present invention comprises water, a pigment, a water-soluble homopolymer and a copolymer having both a hydrophobic portion and a hydrophilic portion.

The present invention can provide a print having excellent density, light fastness and water resistance. Further, the present invention can provide a water-based recording ink having such various properties necessary for use as an ink jet recording ink that it does not clog a fine ejection nozzle, has excellent rubbing resistance and setting to dry in the print, is free from aggregation or settlement of solid matter, such as a pigment particle, and exhibits no change in the properties of the ink even when stored at a high temperature or a low temperature for a long period of time and can be redispersed by stirring or further addition of a solvent even when the pigment once aggregated.

BRIEF DESCRIPTION OF THE DRAWING

The accompanying FIGURE is a diagram showing the structure of a head in an ink jet printer used in an evaluation test for the ink composition according to the present invention.

DETAILED DESCRIPTION OF THE INVENTION

Water-Soluble Homopolymer

Figure 1:
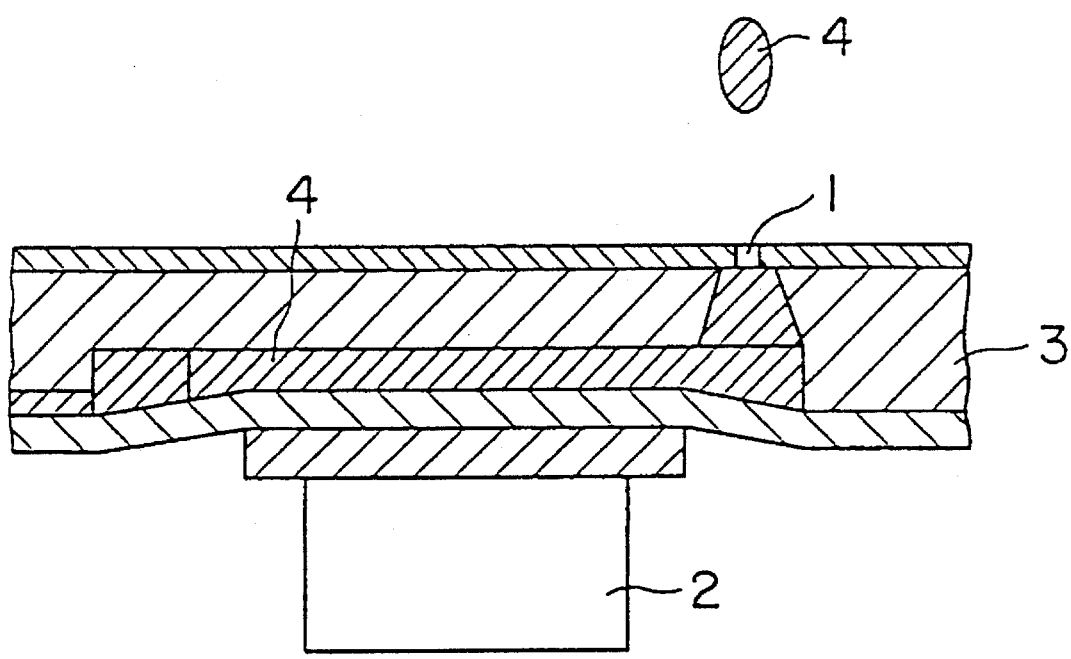

The term "water-soluble homopolymer" contained in the ink of the present invention is intended to mean a water-soluble or aqueous-solution-soluble homopolymer having a polar group (for example, an ionic group, a hydroxyl group, an amino group, an amide group or an ether group). Particularly preferred examples of the water-soluble homopolymer include a homopolymer having such a structure that the above-described polar group is introduced into a polyethylene chain. Preferred examples of the homopolymer include polyalcohols such as polyvinyl alcohol, polyvinyl pyrrolidone and modification products thereof wherein a hydrophilic group, such as a hydroxyl group, a carboxyl group, an ethylene oxide group or an amine group is further introduced.

Still preferred examples of the water-soluble homopolymer used in the present invention include natural polymers such as glue, gelatin, casein, albumin and gum arabic, alginic acid and its derivatives such as alginic acid, propylene glycol alginate, triethanolamine alginate and ammonium alginate, cellulose derivatives such as methyl cellulose, carboxymethyl cellulose, hydroxyethyl cellulose and ethylhydroxyethyl cellulose, polyethylene oxide, polyacrylic acid, sodium polyacrylate, polyvinyl ether, viscose, proteins such as polypeptide, polysaccharides such as starch, guar rubber, a salt of polymethacrylic acid, polyacrylamide, a synthetic resin derived from petroleum, a natural rubber and a glycoside. It is also possible to use them in the form of a mixture of two or more of them.

In the present invention, the weight average molecular weight of the water-soluble homopolymer is preferably 10,000 to 300,000, still preferably 10,000 to 160,000. When the weight average molecular weight is less than 10,000, the water resistance and rubbing resistance of the print may unfavorably lower. On the other hand, when it exceeds 30,000, the storage stability and dispersibility may lower and, in some cases, a failure in ejection of the ink may unfavorably occur due to an increase in the viscosity of the ink.

According to a further preferred embodiment of the present invention, it is preferred to use a water-soluble homopolymer having a solubility of 15% or more in water. This is because a combination of such a water-soluble polymer with the following organic solvent provides a good redispersibility.

Water-Soluble Copolymer

The water-soluble copolymer contained in the ink of the present invention has in its molecule both a hydrophobic portion and a hydrophilic portion. The hydrophobic portion and hydrophilic portion are preferably introduced into the copolymer by copolymerizing a monomer having a hydrophobic group with a monomer having a hydrophilic group.

Preferred examples of the monomer having a hydrophobic group include an unsaturated hydrocarbon, an unsaturated hydrocarbon substituted with a halogen, an unsubstituted carboxylic acid substituted with an alkyl, an alkyl ester, an aryl alkyl ester, an aryl ester or a halogen, an aromatic hydrocarbon, a substituted aromatic hydrocarbon, styrene and its derivative, ethylene and its derivative, and an aliphatic vinyl and its ethylene adduct. Still preferred examples of the monomer include vinyl acetate, acrylonitrile, an alkyl ester of acrylic acid, an alkyl acrylate, butyl acrylate, 1,1,3-trihaloperfluoropropyl acrylate, a dibromopropyl ester of acrylic acid, an ester of acrylic acid, an alkyl methacrylate, an alkyl crotonate, methyl crotonate, glycidyl methacrylate, a hydroxyalkyl ester of methacrylic acid, methyl methacrylate, hydroxyethyl methacrylate, a glycidyl ester of acrylic acid, a dialkylaminoalkyl ester of acrylic acid, a monobutylalkyl ester of maleic acid, an alkyl ester of maleic acid, monobutyl ester of maleic acid, an ester of maleic acid, monomethyl maleate, chloromethylstyrene, polyethylene, divinylbenzene, ethylene dimethacrylate, vinyl crotonate and vinyl propionate.

Preferred examples of the monomer having a hydrophilic group include an unsaturated carboxylic acid and its monoester, amide, salt, etc., and still preferred examples of the monomer include acrylic acid, potassium acrylate, sodium maleaminate, methacrylic acid, maleic acid, maleic anhydride, fumaric acid, itaconic acid, phthalic acid, a monoester of itaconic acid, a monoester of phthalic acid, acrylamide, N-alkylolacrylamide, butoxyacrylamide, methacrylamide, alkylolacrylamide, N-methylolacrylamide, sodium maleaminate, vinylpyrrolidone, N-butoxymethylacrylamide and butoxymethylacrylamide.

Copolymerization of the above-described monomers can provide water-soluble resins having both a hydrophobic portion and a hydrophilic portion. They may be used in the form of a mixture of two or more of them.

In the present invention, the weight average molecular weight of the water-soluble resin is preferably 1,000 to 100,000, still preferably 1,000 to 50,000. When it is smaller than 1,000, the dispersion stability of the pigment particle may unfavorably lower. On the other hand, when it exceeds 100,000, the solubility in water may lower and cause the storage stability to be lowered, so that clogging occurs.

In particular, a resin having a HLB value of 4 or more is preferred, and the HLB value is still preferably 10 or more. When the HLB value is 4 or more, the adsorption of the resin to the pigment particle becomes suitable, which favorably contributes to an improvement in the dispersion stability.

Ink Composition

The water-soluble homopolymer and copolymer having both a hydrophilic portion and a hydrophilic portion may be considered to play the following role in the ink composition of the present invention although the reason is not bound by the following theory. Specifically, at the outset, the copolymer having both a hydrophilic portion and a hydrophobic portion is adsorbed on the surface of a pigment as a coloring material to stabilize the pigment. Further, the water-soluble homopolymer forms a protective layer around the pigment particle stabilized by the copolymer. Thus, the dispersibility and storage stability of the pigment particle in the ink can be improved by the above double layer. It is also considered that the homopolymer and copolymer not adsorbed to the pigment serve to improve the fixability of the pigment particle onto a transfer material.

The ink composition according to the present invention has an improved capability of wetting a head material comprising a plastic, a metal or a ceramic while preventing the occurrence of bubbles. This property improves the outflow, flowability and wettability of the ink in the head and eliminates causes of failure in the ejection, such as occurrence of bubbles. Further, a change in the viscosity and surface tension of the ink with the temperature can be inhibited, and the drying rate of the ink lowers. This ensures adaptability to a wide range of a change in the environment in respect of the temperature and humidity.

On the other hand, when the two water-soluble resins are not contained, the above property requirements cannot be satisfied.

Therefore, the incorporation of the two water-soluble resins contributes to the attainment of the object of the present invention, that is, no aggregation and settlement of the coloring material particles, no change in the properties of the ink and no precipitation of solid matter during storage at a high or low temperature for a long period of time; no deterioration in the dispersion stability and storage stability even when a solvent or the like is subsequently added; and an improvement in the rubbing resistance-and the prevention of clogging by virtue of imparting the redispersibility.

The incorporation of the above two water-soluble resins has a further effect of permitting the ink to easily wet an ink jet head and an ink feed passage, so that it becomes possible to smoothly feed the ink and, at the same time, to remove bubbles which may cause a failure in the ejection of the ink.

It is preferred for the water-based recording ink of the present invention to contain the water-soluble homopolymer, the water-soluble copolymer and other component according to the following formulation.

The amount of the water-soluble homopolymer in the ink composition is preferably 0.8 to 30% by weight, still preferably 2 to 10% by weight. When the amount is less than 0.8% by weight, no desired effect may be attained. On the other hand, when it exceeds 30% by weight, the viscosity of the ink composition may increase. Furthermore, the amount of the homopolymer is preferably 20% by weight or more based on one part of the following pigment as the coloring material from the viewpoint of the storage stability and dispersion stability of the ink.

The amount of the copolymer having both a hydrophobic portion and a hydrophilic portion is preferably 0.1 to 1.5% by weight, still preferably 0.1 to 1.0% by weight. When the amount is smaller than 0.1% by weight, no desired effect may be attained and, in some cases, the fixability of the pigment particle onto a transfer material may unfavorably lower. On the other hand, when it exceeds 1.5% by weight, clogging may be unfavorably liable to occur.

There is no particular limitation on the pigment as a coloring material according to the present invention so far as it has a good affinity for water as a main solvent. Examples of the pigment for a black-and-white ink include carbon black such as furnace black, lamp black, acetylene black, channel black, metals such as copper, iron and titanium oxide, and organic pigments such as o-nitroaniline black. Examples of the pigment for a color ink include toluidine red, permanent carmine FB, fast yellow AAA, disazo orange PMP, lake red C, brilliant carmine 6B, phthalocyanine blue, quinacridone red, dioxane violet, victoria pure blue, alkali blue toner, fast yellow 10G, disazo yellow AAMX, disazo yellow AAOT, disazo yellow AAOA, yellow iron oxide, disazo yellow HR, o-nitroaniline orange, dinitroaniline orange, vulcan orange, toluidine red, chlorinated para red, brilliant fast scarlet, naphthol red 23, pyrazolone red, barium red 2B, calcium red 2B, strontium red 2B, manganese red 2B, barium lithol red, pigment scarlet 3B lake, lake bordeaux 10B, anthocyan 3B lake, anthocyan 5B lake, rhodamine 6G lake, eosine lake, iron oxide red, fastol red FGR, rhodamine B lake, methyl violet lake, dioxadine violet, basic blue 5B lake, basic blue 6G lake, fast sky blue, alkali blue R toner, peacock blue lake, iron blue, ultramarine blue, reflex blue 2G, reflex blue R, brilliant green lake, diamond green thioflavine lake, phthalocyanine green G, green gold, phthalocyanine green Y, iron oxide powder, tarnish, zinc flower, titanium oxide, calcium carbonate, clay, barium sulfate, alumina white, aluminum powder, bronze powder, daylight fluorescent pigment, pearl pigment, naphthol carmine FB, naphthol red M, permanent carmine FB, fast yellow G, disazo yellow AAA, disazo orange PMP, lake red C, dioxane violet, alkali blue G toner and processed pigments, such as graft carbon having a surface treated with a resin or the like.

The amount of the pigment is preferably 1 to 30% by weight, still preferably 4 to 10% by weight. The particle diameter of the pigment is preferably 25 μm or less, still preferably 1 μm or less.

According to a further preferred embodiment of the present invention, it is preferred to further incorporate a high-boiling, low-volatile solvent and a monohydric alcohol in the ink. The incorporation of the high-boiling, low-volatile solvent in the ink contributes to an improvement in the wettability of the ink and, at the same time, enables the pigment to be easily redispersed by adding water even when water has been evaporated. It can be expected that this prevents the clogging of the nozzle. The incorporation of the monohydric alcohol in the ink also contributes to an improvement in the quick drying property and fixability of the ink while preventing the clogging of the nozzle. Furthermore, it is possible to attain an improvement in the matching between the head and the ink (specifically an improvement in the capability of the ink to wet the head, easy discharge of bubbles and an improvement in the flowability of the ink, etc.). The co-existence of the high-boiling, low-volatile solvent and the monohydric alcohol can prevent the clogging of the nozzle attributable to drying of the ink within the nozzle and, at the same time, can impart such a property that the print can dry immediately after printing.

Preferred examples of the high-boiling, low-volatile solvent used in the present invention include polyhydric alcohols such as glycerin, ethylene glycol, diethylene glycol, triethylene glycol, propylene glycol, polyethylene glycol and 1,5-pentanediol and their monoetherification products, dietherification products and esterification products, for example, ethylene glycol monomethyl ether, ethylene glycol monoethyl ether, ethylene glycol monobutyl ether, diethylene glycol monomethyl ether, diethylene glycol monoethyl ether and diethylene glycol monobutyl ether, and nitrogen-containing organic solvents such as N-methyl-2-pyrrolidone and 1,3-dimethylimidazolidinone.

The amount of the high-boiling, low-volatile solvent is preferably 0.45 to 20% by weight, still preferably 2 to 10% by weight. Furthermore, it is preferred from the viewpoint of preventing the clogging and ensuring quick drying of the ink on a transfer material that this high-boiling, low-volatile solvent be added in an amount of 0.5 to 5 parts by weight based on one part by weight of the pigment.

Preferred examples of the monohydric alcohol used in the present invention include ethanol, 1-propanol, 2-propanol, 1-butanol and 2-butanol.

The amount of the monohydric alcohol is preferably 0.5 to 30% by weight, still preferably 2 to 12% by weight. Furthermore, it is preferred that the monohydric alcohol be added in an amount of 0.5 to 3% by weight based on one part of the pigment. This contributes to an improvement in the storage stability of the ink and quick drying of the ink on a transfer material.

The ink composition according to the present invention can include a third component so far as the effect of the present invention is not spoiled. Examples of the third component include surfactants, mildewproofing agents, pH adjustors such as potassium dihydrogenphosphate and sodium dihydrogenphosphate, and additives for mildewproofing, antiseptic and rust preventing purposes, such as benzoic acid, dichlorophene, hexachlorophene, sorbic acid, an ester of p-hydroxybenzoic acid and ethylenediaminetetraacetic acid (EDTA). It is also possible to add urea, thiourea, ethyleneurea, etc. for the purpose of preventing the nozzle from drying.

In the ink composition of the present invention, the above-described components are dispersed according to a conventional method and optionally filtered by means of a filter to remove foreign matter and coarse particles. It is also preferred that the ink composition of the present invention be produced by a method including at least one treatment step selected from filtration under pressure, filtration under reduced pressure and centrifugation.

The ink composition of the present invention according to the above-described formula can realize the attainment of various properties generally required of an ink jet recording ink, that is, a viscosity of 1 to 20 mpa·sec (at room temperature), still preferably 2 to 8 mpa·sec, a surface tension of 40 to 70 mN/m (room temperature) and a pH value of 4 to 8.

The ink composition of the present invention can be used in a temperature region where an ink jet printer is usually employed, that is, at a temperature in the range of from −20° to 70° C. without occurrence of a precipitate and deterioration in the ink, etc.

The ink according to the present invention can cope with color printing and be used in a color printer (a plurality of colors or a full color).

EXAMPLES

The present invention will now be described in more detail with reference to the following Examples, though it is not limited to these Examples.

In the following Examples, the term "water-soluble resin 1" is intended to mean a water-soluble homopolymer, and the term "water-soluble resin 2" is intended to mean a copolymer having both a hydrophobic portion and a hydrophilic portion. The numeral used for expressing the composition ratio is % by weight.

Example 1

An ink having the following composition was produced.

| Component | Composition Ratio |
| --- | --- |
| CB (MA-100) | 5 |
| Water-soluble resin 1 (PVP; Mw = 40,000) | 3 |
| Water-soluble resin 2 (acrylic acid/acrylonitrile copolymer) | 0.3 |
| Glycerin | 5 |
| Ethanol | 5 |
| 1,2-Benzoisothiazolin-3-one | 0.03 |
| Propylene glycol | 0.3 |
| Water | 81.37 |

MA-100 is a carbon black manufactured by Mitsubishi Kasei Industries, Ltd., and PVP (K-30) used as the water-soluble resin 1 is a polyvinyl pyrrolidone having a weight average molecular weight of about 40,000 and manufactured by Tokyo Kasei Co., Ltd.

The production of the ink was conducted according to the following procedure. The carbon black and the water-soluble resin 2 were mixed with each other in water while stirring by means of a paint shaker for 30 min or more. After it was confirmed by observation under a microscope that the particle diameter was reduced to 1 μm or less, polyvinyl pyrrolidone was added. The mixture was further mixed with stirring for 30 min for complete dissolution filtered unde pressure by means of a 3-μmm membrane of polyvinyl pyrrolidone. The resultant dispersion was filter and/or a 5-μm metallic filter to remove foreign particles and coarse particles. Then, glycerin and ethanol were added thereto, and the mixture was stirred for 5 min to provide a water-based recording ink having a particle diameter of 0.06 μm in the particulate component and a pH value of 7.

Ink compositions of Examples 2 to 10 and Comparative Examples 1 to 6 were prepared in substantially the same manner as that of Example 1.

Example 2

| Component | Composition Ratio |
| --- | --- |
| CB (MA-100) | 4 |
| Water-soluble resin 1 (PVP; Mw = 10,000) | 5.8 |
| Water-soluble resin 2 (potassium acrylate/acrylonitrile copolymer) | 0.2 |
| Triethylene glycol | 6 |
| 1-Propanol | 2 |
| Ethanol | 3 |
| Water | 79 |

MA-100 is a carbon black manufactured by Mitsubishi Kasei Industries, Ltd., and PVP (K-15) used as the water-soluble resin 1 is a polyvinyl pyrrolidone having a weight average molecular weight of about 10,000 and manufactured by Tokyo Kasei Co., Ltd.

The ink thus prepared had an average particle diameter of 0.2 μm in the particulate component and a pH value of 6.8.

Example 3

| Component | Composition Ratio |
| --- | --- |
| CB (MA-11) | 5 |
| Water-soluble resin 1 (PVP; Mw = 160,000) | 2 |
| Water-soluble resin 2 (styrene/maleic acid copolymer) | 0.5 |
| Ethylene glycol | 16 |
| 1-Butanol | 8 |
| Water | 68.5 |

MA-11 is a carbon black manufactured by Mitsubishi Kasei Industries, Ltd., and PVP (K-60) used as the water-soluble resin 1 is a polyvinyl pyrrolidone having a weight average molecular weight of about 160,000 and manufactured by Tokyo Kasei Co., Ltd.

The ink thus prepared had an average particle diameter of 0.15 μm in the particulate component.

Example 4

| Component | Composition Ratio |
| --- | --- |
| CB (Vulcan sc) | 5 |
| Water-soluble resin 1 (PVP; Mw = 40,000) | 6 |
| Water-soluble resin 2 (styrene-acrylic acid/ethyl acrylate copolymer) | 0.5 |
| Glycerin | 8 |
| 2-Butanol | 6 |
| Water | 74.5 |

Vulcan sc is a carbon black manufactured by Cabot Corporation, and PVP (K-30) used as the water-soluble resin 1 is a polyvinyl pyrrolidone having a weight average molecular weight of about 40,000 and manufactured by Tokyo Kasei Co., Ltd.

The ink thus prepared had an average particle diameter of 0.09 μm in the particulate component.

Example 5

| Component | Composition Ratio |
| --- | --- |
| CB (RAVEN 150) | 6 |
| Water-soluble resin 1 (PVP; Mw = 20,000) | 6 |
| Water-soluble resin 2 (styrene/acrylic acid copolymer) | 0.3 |
| Polyethylene glycol | 8 |
| 1-Propanol | 5.5 |
| Water | 74.2 |

RAVEN 150 is a carbon black manufactured by Columbian Carbon Co. Ltd., and polyvinyl alcohol (B-03) used as the water-soluble resin 1 is a polyvinyl pyrrolidone manufactured by Denki Kagaku Kogyo K.K.

The ink thus prepared had an average particle diameter of 0.25 μm in the particulate component.

Example 6

| Component | Composition Ratio |
| --- | --- |
| Pigment (KETRed 309) | 5 |
| Water-soluble resin 1 (PVP; Mw = 40,000) | 3 |
| Water-soluble resin 2 (styrene/maleic acid copolymer) | 0.3 |
| Glycerin | 5 |
| Ethylene glycol | 1 |
| Polyethylene glycol (#200) | 1 |
| 2-Propanol | 5 |
| Water | 79.7 |

KETRed 309 is an organic pigment for a color toner manufactured by Dainippon Ink & Chemicals, Inc.

The ink thus prepared had an average particle diameter of 0.09 μm in the particulate component.

Example 7

| Component | Composition Ratio |
| --- | --- |
| Pigment (KETYELLOW 403) | 5 |
| Water-soluble resin 1 (PVP; Mw = 40,000) | 3 |
| Water-soluble resin 2 (diisobutylene/maleic acid copolymer) | 0.3 |
| Ethanol | 8 |
| Glycerin | 10 |
| Diethylene glycol | 2 |
| Ethylene glycol | 5 |
| Water | 66.7 |

KETYELLOW 403 is an organic pigment for a color toner manufactured by Dainippon Ink & Chemicals, Inc.

Besides the above components, a small amount of Proxel XL2 (manufactured by ICI) was added as an antiseptic.

The ink thus prepared had an average particle diameter of 0.15 μm in the particulate component.

Example 8

| Component | Composition Ratio |
|---|---|
| Pigment (KETBLUE Ex-1) | 5 |
| Water-soluble resin 1 (PVP; Mw = 40,000) | 3 |
| Water-soluble resin 2 (styrene/maleic acid half ester/maleic anhydride copolymer) | 0.3 |
| Diethylene glycol | 4 |
| Ethanol | 5 |
| Water | 82.7 |

KETBLUE Ex-1 is an organic pigment for a color toner manufactured by Dainippon Ink & Chemicals, Inc.

Besides the above components, a small amount of Trilon BS (EDTA manufactured by BASF) was added as an antiseptic.

The ink thus prepared had an average particle diameter of 0.1 μm in the particulate component.

Example 9

| Component | Composition Ratio |
|---|---|
| CB (MCF-88) | 5 |
| Water-soluble resin 1 (PVP; Mw = 40,000) | 3 |
| Water-soluble resin 1 (PVP; Mw = 20,000) | 1 |
| Water-soluble resin 2 (Acrylic acid/Acrylonitrile copolymer) | 0.8 |
| Glycerin | 5 |
| Ethanol | 3 |
| 2-Propanol | 3 |
| Water | 79.2 |

MCF-88 is a carbon black manufactured by Mitsubishi Kasei Industries, Ltd., and PVP used as the water-soluble resin 1 is a polyvinyl pyrrolidone having a weight average molecular weight of about 40,000 and manufactured by Tokyo Kasei Co., Ltd., and PVA is a polyvinyl alcohol having a weight average molecular weight of about 20,000 and manufactured by Denki Kagaku Kogyo K.K.

The ink thus prepared had an average particle diameter of 0.14 μm in the particulate component.

Example 10

| Component | Composition Ratio |
|---|---|
| CB (MA-100) | 5 |
| Water-soluble resin 1 (PVP; Mw = 40,000) | 2 |
| Water-soluble resin 1 (PVP; Mw = 20,000) | 3 |
| Water-soluble resin 2 (Acrylic acid/Acrylonitrile copolymer) | 0.8 |
| Water-soluble resin 2 (Potassium acrylate/Acrylonitrile copolymer) | 0.1 |
| Glycerin | 5 |
| Ethylene glycol | 2 |
| 1-Propanol | 4 |
| Water | 78.1 |

MA-100 is a carbon black manufactured by Mitsubishi Kasei Industries, Ltd., and PVP used as the water-soluble resin 1 is a polyvinyl pyrrolidone, having a weight average molecular weight of about 40,000 and manufactured by Tokyo Kasei Co., Ltd., and PVA is a polyvinyl poval having a weight average molecular weight of about 20,000 and manufactured by Denki Kagaku Kogyo K.K.

The ink thus prepared had an average particle diameter of 0.09 μm in the particulate component.

Comparative Example 1

| Component | Composition Ratio |
|---|---|
| CB (MCF-88) | 5 |
| Water-soluble resin 2 (Styrene/Acrylic acid copolymer) | 4 |
| Glycerin | 8 |
| Ethylene glycol | 12 |
| Ethanol | 5 |
| Monoethanolamine | 0.4 |
| Water | 65.6 |

This Comparative Example 1 is an example of the ink composition containing the water-soluble resin 2 alone.

Comparative Example 2

| Component | Composition Ratio |
|---|---|
| CB (MA-100) | 5 |
| Water-soluble resin 1 (PVP; Mw = 40,000) | 4 |
| Glycerin | 2 |
| Ethanol | 5 |
| Water | 84 |

In the Comparative Example 2, the ink composition contains the water-soluble resin 1 alone.

Comparative Example 3

| Component | Composition Ratio |
|---|---|
| CB (MA-100) | 6 |
| Water-soluble resin 1 (PVP; Mw = 10,000) | 3 |
| Nonionic dispersant (S-381) | 0.8 |
| Glycerin | 10 |
| 1,3-dimethylimidazolidinone | 5 |
| Water | 75.2 |

In the Comparative Example 3, the ink composition contains the water-soluble resin 1 alone.

Comparative Example 4

| Component | Composition Ratio |
|---|---|
| CB (KETRed 309) | 5 |
| Water-soluble resin 1 (PVP; Mw = 40,000) | 4 |
| Water-soluble resin 1 (B-03 Mw = 20,000) | 2 |
| Glycerin | 2 |
| Butanol | 5 |
| Water | 82 |

In the Comparative Example 4, the ink composition contains two kinds of water-soluble resins 1.

Comparative Example 5

| Component | Composition Ratio |
| --- | --- |
| CB (KETYELLOW 403) | 6 |
| Water-soluble resin 2 | 0.8 |
| (Acrylic acid/acrylonitrile copolymer) | |
| Glycerin | 5 |
| 1-Propanol | 4 |
| Water | 84.1 |

In the Comparative Example 5, the ink composition contains two kinds of water-soluble resins 2.

Comparative Example 6

| Component | Composition Ratio |
| --- | --- |
| CB (KETBLUE Ex-1) | 6 |
| Water-soluble resin 1 | 0.1 |
| (B-03; Mw = 20,000 copolymer) | |
| Water-soluble resin 2 | 0.5 |
| (Acrylic acid/acrylonitrile copolymer) | |
| Glycerin | 3 |
| Ethanol | 10 |
| Water | 80.4 |

In the Comparative Example 6, the ink composition contains the water-soluble resins 1 and 2 each in an amount of less than 2% by weight.

Printing Test

Ink compositions prepared in Examples 1 to 10 and Comparative Examples 1 to 6 were subjected to a printing test.

The printing test was conducted through the use of an ink jet printer provided with a head having a structure shown in FIG. 1. This head has such a structure that a pressure generating member 2 comprising a laminated piezoelectric element is bonded to the wall surface of a cavity 3. The pressure generating member (laminated piezoelectric element) 2 bends due to an applied voltage during driving, and the ink within the cavity is pressurized, which causes an ink droplet 4 to be jetted from a nozzle 1. The diameter of the jetting nozzle of the ink jet printer head used in the test is 50 μm, and the piezoelectric element driving voltage, driving frequency and resolution were 50 V, 2 kHz and 300 dots/inch, respectively. PPC paper manufactured by Xerox Corp. was used as the recording paper.

The evaluation of the resultant print was conducted in terms of the following 8 items.

Evaluation 1: The quality of the print sample was observed under a microscope (magnification:×200).

Evaluation 2: The ink was allowed to stand at 40° C. for 3 days and then immediately examined on whether or not printing could be conducted without clogging.

Evaluation 3: Solid printing was conducted, and the print was allowed to stand for 2 hr. Thereafter, the print was strongly rubbed with a finger to evaluate whether or not the print was peeled off.

Evaluation 4: Immediately after solid printing, another recording paper was put on the printed surface of recorded paper to determine a time taken for no ink to be transferred, thereby evaluating quick drying property of the ink.

Evaluation 5: Printing was continuously conducted for 12 hr, and dropout of dots was examined during the printing to evaluate jetting stability.

Evaluation 6: The ink was allowed to stand at room temperature for one month, and the degree of aggregation of the pigment particle was then observed under a microscope to evaluate storage stability.

Evaluation 7: The ink was hermetically sealed into a sample bottle made of a glass and subjected to a heat cycle wherein it was allowed to stand alternatively at an environmental temperature of −20° C. and an environmental temperature of 60° C. for 7 days. Thereafter, the degree of aggregation of the pigment particle in the ink was observed under a microscope.

Evaluation 8: Superimposition printing was conducted through the use of various color inks to evaluate the quality of the color print.

The results of evaluation are given in Table 1.

TABLE 1

| Name of ink | Evaluation 1 Quality of print | Evaluation 2 Clogging | Evaluation 3 Rubbing resistance | Evaluation 4 Quick drying | Evaluation 5 Jetting stability | Evaluation 6 Storage stability | Evaluation 7 Heat cycle | Evaluation 8 Color printing |
| --- | --- | --- | --- | --- | --- | --- | --- | --- |
| Ex. | | | | | | | | |
| 1 | ⊙ | ⊙ | ⊙ | ⊙ | ⊙ | ⊙ | ⊙ | |
| 2 | ⊙ | ⊙ | ⊙ | ⊙ | ⊙ | ⊙ | ⊙ | |
| 3 | ⊙ | ⊙ | ⊙ | ⊙ | ⊙ | ⊙ | ⊙ | |
| 4 | ⊙ | ⊙ | ⊙ | ⊙ | ⊙ | ⊙ | ⊙ | |
| 5 | ⊙ | ⊙ | ⊙ | ⊙ | ⊙ | ⊙ | ⊙ | |
| 6 | ⊙ | ⊙ | ⊙ | ⊙ | ⊙ | ⊙ | ⊙ | ⊙ |
| 7 | ⊙ | ⊙ | ⊙ | ⊙ | ⊙ | ⊙ | ⊙ | ⊙ |
| 8 | ⊙ | ⊙ | ⊙ | ⊙ | ⊙ | ⊙ | ⊙ | ⊙ |
| 9 | ⊙ | ⊙ | ⊙ | ⊙ | ⊙ | ⊙ | ⊙ | |
| 10 | ⊙ | ⊙ | ⊙ | ⊙ | ⊙ | ⊙ | ⊙ | |
| Comp. Ex. | | | | | | | | |
| 1 | | o | x | o | x | x | x | x |
| 2 | ⊙ | x | x | x | x | x | x | |
| 3 | x | o | x | x | x | x | x | |

TABLE 1-continued

| Name of ink | Evaluation 1 Quality of print | Evaluation 2 Clogging | Evaluation 3 Rubbing resistance | Evaluation 4 Quick drying | Evaluation 5 Jetting stability | Evaluation 6 Storage stability | Evaluation 7 Heat cycle | Evaluation 8 Color printing |
|---|---|---|---|---|---|---|---|---|
| 4 | ◉ | x | ◉ | x | x | x | x | o |
| 5 | o | x | x | x | x | x | x | o |
| 6 | x | x | x | x | x | x | x | o |

Symbols in the Table represent the following results of evaluation.

◉: Excellent, and no problem (drying time: 15 to 30 sec)

○: Small problem (drying time: 30 to 60 sec)

×: Poor, and serious problem (drying time: 60 sec or more)

The ink composition of the present invention provided a high-quality print free from bleeding. Further, it had a quick drying of about 15 to 30 sec, that is, a quick drying remarkably improved over the conventional ink which had a quick drying of 30 sec to 1 min. Furthermore, according to the ink composition of the present invention, the fixability as well is satisfactory, and the jetting stability and storage stability as well were good.

The water-based recording ink of the present invention was also subjected to an evaluation of the quality of printing through the use of recycled paper, i.e., new CK paper and R paper manufactured by Xerox Corp., and a yamayuri paper manufactured by Honshu Paper Co., Ltd. As a result, with respect to the three recycled paper as well, a print having no significant bleeding, i.e., a good printing quality, could be obtained.

Then, a color pattern was printed by superimposition printing of three colors through the use of three kinds of color inks described in Examples 6 to 8. The resultant image was free from bleeding and diffusion of inks into each other and sharp.

We claim:

1. An ink composition for use in ink jet recording, said composition comprising water, a water-soluble homopolymer, a water-soluble copolymer having both a hydrophobic portion and a hydrophilic portion, and a pigment dispersible in said composition, said water-soluble homopolymer and water-soluble copolymer being present in said composition in respective amounts sufficient to improve dispersion stability of said pigment in said composition, with said water-soluble copolymer being present in the composition in an amount of between 0.1 to 1.5 weight percent.

2. An ink composition according to claim 1, wherein the homopolymer has an average molecular weight of 10,000 or more.

3. An ink composition according to claim 1, wherein the homopolymer is polyvinyl pyrrolidone or polyvinyl alcohol.

4. An ink composition according to claim 1, wherein the homopolymer is present in an amount of from about 0.8 to 30 wt. % of the ink and about 20 weight % or more based on the pigment.

5. An ink composition according to claim 1, which comprise 2 wt. % or more of the homopolymer and the copolymer.

6. An ink composition according to claim 1, which further comprises a high-boiling, low-volatile solvent and a monohydric alcohol.

7. An ink composition according to claim 6, wherein the high-boiling, low-volatile solvent is selected from the group consisting of glycerin, ethylene glycol, diethylene glycol, triethylene glycol, propylene glycol and polyethylene glycol.

8. An ink composition according to claim 7, which comprises 0.45 to 20 wt. % of the high-boiling, low-volatile solvent.

9. An ink composition according to claim 7, wherein the monohydric alcohol is selected from the group consisting of ethanol, 1-propanol, 2-propanol and butanol.

10. An ink composition according to claim 7, which comprises 0.5 to 30 wt. % of the monohydric alcohol.

11. An ink composition according to claim 1, which comprises 1 to 30 wt. % of the pigment.

12. An ink composition as claimed in claim 6 wherein the composition consists essentially of the water, the water-soluble homopolymer, the water-soluble copolymer, the pigment, the high-boiling, low-volatile solvent and the monohydric alcohol.

13. In an ink-jet recording process which comprises forcing droplets of an ink composition out of a nozzle and recording on an image receiving material by using the droplets, the improvement comprising forming the droplets from the ink composition of claim 6.

14. An ink composition as claimed in claim 1 wherein the composition consists essentially of the water, the water-soluble homopolymer, the water-soluble copolymer and the pigment.

15. An ink composition according to claim 1, wherein the water-soluble homopolymer has a solubility of 15% or more in water, the water-soluble copolymer has an average molecular weight of 1,000 to 50,000, the amount of homopolymer is 0.8 to 30 wt % of the ink composition and 20 weight % or more based on the pigment, and the amount of the copolymer is 0.1 to 1.5 wt % of the ink composition.

16. In an ink-jet recording process which comprises forcing droplets of an ink composition out of a nozzle and recording on an image receiving material by using the droplets, the improvement comprising forming the droplets from the ink composition of claim 15.

17. In an ink-jet recording process which comprises forcing droplets of an ink composition out of a nozzle and recording on an image receiving material by using the droplets, the improvement comprising forming the droplets from the ink composition of claim 1.

18. An ink composition as claimed in claim 1, wherein the water-soluble copolymer is produced by copolymerizing a monomer having a hydrophobic group with a monomer having a hydrophilic group.

19. An ink composition according to claim 18 wherein the monomer having a hydrophilic group comprises acrylic acid or acrylate and the monomer having a hydrophobic group comprises acrylonitrile.

20. An ink composition as claimed in claim 1, wherein the amount of said water-soluble homopolymer is 20 weight percent or more based on said pigment.

21. An ink composition as claimed in claim 1, wherein the amount of said water-soluble homopolymer has a solubility of 15% or more in water.

22. An ink composition for use in ink jet recording, said composition consisting essentially of water, a water-soluble homopolymer, a water-soluble copolymer having both a hydrophobic portion and a hydrophilic portion, a pigment dispersible in said composition, a high-boiling, low volatile solvent and a monohydric alcohol, said water-soluble homopolymer, water-soluble copolymer, solvent and alcohol being present in said composition in respective amounts such that, upon an evaporation of the water, the pigment is redispersible with an addition of more water.

23. An ink composition as claimed in claim 22, wherein the high-boiling, low-volatile solvent is selected from the group consisting of glycerin, ethylene glycol, propylene glycol and polyethylene glycol.

24. An ink composition according to claim 22, which comprises 0.45 to 20 weight percent of the high-boiling, low-volatile solvent.

25. An ink composition according to claim 22, wherein the monohydric alcohol is selected from the group consisting of ethanol, 1-propanol, 2-propanol and butanol.

26. An ink composition according to claim 24, which comprises 0.5 to 30 weight percent of the monohydric alcohol.

27. An ink composition according to claim 26, which comprises 1 to 30 weight percent of the pigment.

28. An ink composition for use in ink jet recording wherein droplets of the composition are jetted onto a recording medium to form print dots on the medium, the composition comprising water, a water-soluble homopolymer, a water-soluble copolymer having both a hydrophobic portion and a hydrophilic portion, and a pigment dispersible in said composition, said water-soluble homopolymer and water-soluble copolymer being present in said composition in respective amounts sufficient to improve jetting stability of said composition such that said droplets can be jetted onto said medium substantially without dropout of the dots, said water-soluble copolymer being present in the composition in an amount of between 0.1 to 1.5 weight percent.

* * * * *